United States Patent
Schmalhurst et al.

(10) Patent No.: US 9,402,463 B2
(45) Date of Patent: Aug. 2, 2016

(54) ADAPTIVE SYSTEM FOR MODIFYING USER BRUSHING SYSTEM

(71) Applicant: KONINKLIJKE PHILIPS N.V., Eindhoven (NL)

(72) Inventors: Lisa Bethany Schmalhurst, Issaquah, WA (US); Kevin Arnold Miller, Bellevue, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/651,242

(22) PCT Filed: Dec. 17, 2013

(86) PCT No.: PCT/IB2013/061008
§ 371 (c)(1),
(2) Date: Jun. 11, 2015

(87) PCT Pub. No.: WO2014/097129
PCT Pub. Date: Jun. 26, 2014

(65) Prior Publication Data
US 2015/0313353 A1    Nov. 5, 2015

Related U.S. Application Data

(60) Provisional application No. 61/740,830, filed on Dec. 21, 2012.

(51) Int. Cl.
*A46B 15/00* (2006.01)
*A61C 17/22* (2006.01)

(52) U.S. Cl.
CPC ......... *A46B 15/0012* (2013.01); *A46B 15/0006* (2013.01); *A46B 15/0044* (2013.01); *A61C 17/221* (2013.01)

(58) Field of Classification Search
CPC ........... A46B 15/0012; A46B 15/0006; A46B 15/0002; A46B 15/0044; A61C 17/221
See application file for complete search history.

(56) References Cited

U.S. PATENT DOCUMENTS

| | | |
|---|---|---|
| 5,337,435 A | 8/1994 | Krasner et al. |
| 5,784,742 A | 7/1998 | Giuliani et al. |
| 5,924,159 A | 7/1999 | Haitin |
| 6,536,068 B1 | 3/2003 | Yang et al. |
| 7,383,603 B2 | 6/2008 | Edwards |
| 2003/0115693 A1 | 6/2003 | Grez et al. |
| 2003/0205492 A1 | 11/2003 | Ferber et al. |
| 2005/0015906 A1 | 1/2005 | Baglieri |
| 2009/0038639 A1 | 2/2009 | Yetukuri et al. |
| 2009/0130636 A1 | 5/2009 | Hwang |
| 2009/0307859 A1 | 12/2009 | Mottram et al. |
| 2009/0320227 A1 | 12/2009 | Cohen et al. |
| 2010/0015589 A1 | 1/2010 | Lehavi |
| 2010/0106336 A1 | 4/2010 | Hwang et al. |
| 2010/0323337 A1 | 12/2010 | Ikkink et al. |

FOREIGN PATENT DOCUMENTS

DE    198440684 A1    3/2000

*Primary Examiner* — Shay Karls

(57) ABSTRACT

The adaptive system includes a power toothbrush (10) which determines bristle force or pressure applied by the user against the teeth. The toothbrush includes a processing system (28) for comparing the determined force with a threshold value of excessive force and a threshold adaptive value which is below the excessive force threshold but serves as a warning for the user. The system is capable of raising the initial adaptive value threshold (64) following the user exceeding the adaptive value for a selected number of brushing events and then further for decreasing the adaptive value (66) back toward the initial adaptive value when the increased adaptive value is not exceeded for a selected number of brushing events, thus providing the ability to encourage/coach the user toward a brushing force which is below the threshold adaptive level and into a safe region of operation.

7 Claims, 2 Drawing Sheets

A ADAPTIVE SYSTEM FOR MODIFYING USER BRUSHING SYSTEM

CROSS-REFERENCE TO PRIOR APPLICATIONS

This application is the U.S. National Phase application under 35 U.S.C. §371 of International Application No. PCT/IB2013/061008, filed on Dec. 17, 2013, which claims the benefit of U.S. Provisional Patent Application No. 61/740,830, filed on Dec. 21, 2012. These applications are hereby incorporated by reference herein.

TECHNICAL FIELD

This invention relates generally to power toothbrushes which provide information to the user concerning the force applied to the teeth during brushing action, and more specifically concerns a system for providing such information in a manner as to influence a change in the user's brushing behavior.

BACKGROUND OF THE INVENTION

Force sensors are used in power toothbrushes to provide load information to the user. The information is used to maintain the force within an effective range and prevent the use of excessive force, which is harmful to the gums of the user, or too little force, wherein results in ineffective cleaning. While an indication of excessive force is often effective in assisting a user to operate the brush properly at correct force, in some cases, an indication of excessive force to the user produces little or no change on the part of the user. This leads to harm to the gums or other tissues of the user and can also result in the user terminating use of the toothbrush, thereby foregoing the effective cleansing results of a power toothbrush.

Accordingly, it is desirable to have a load pressure indication system in a power toothbrush which has a coaching or tutoring effect for the user, helping the user to reduce the force on the teeth to a safe load.

SUMMARY OF THE INVENTION

Accordingly, the adaptive system for modifying user brushing action comprises: a power toothbrush which includes a system for determining the bristle force applied by the user against the user's teeth; a processing system for comparing the determined force against a threshold value of excessive force and a threshold adaptive value which is below the excessive force threshold, the processing system raising the adaptive value following the user exceeding the adaptive value for a selected number of brushing events and then for decreasing the adaptive value back toward the threshold adaptive value when the adaptive value is not exceeded for a selected number of brushing events; and an indication system for communicating information to the user when the force applied is at a safe level of force, at an excessive force level, and when the adaptive value of force has been reached.

BEST MODE FOR CARRYING OUT THE INVENTION

Figure 1:
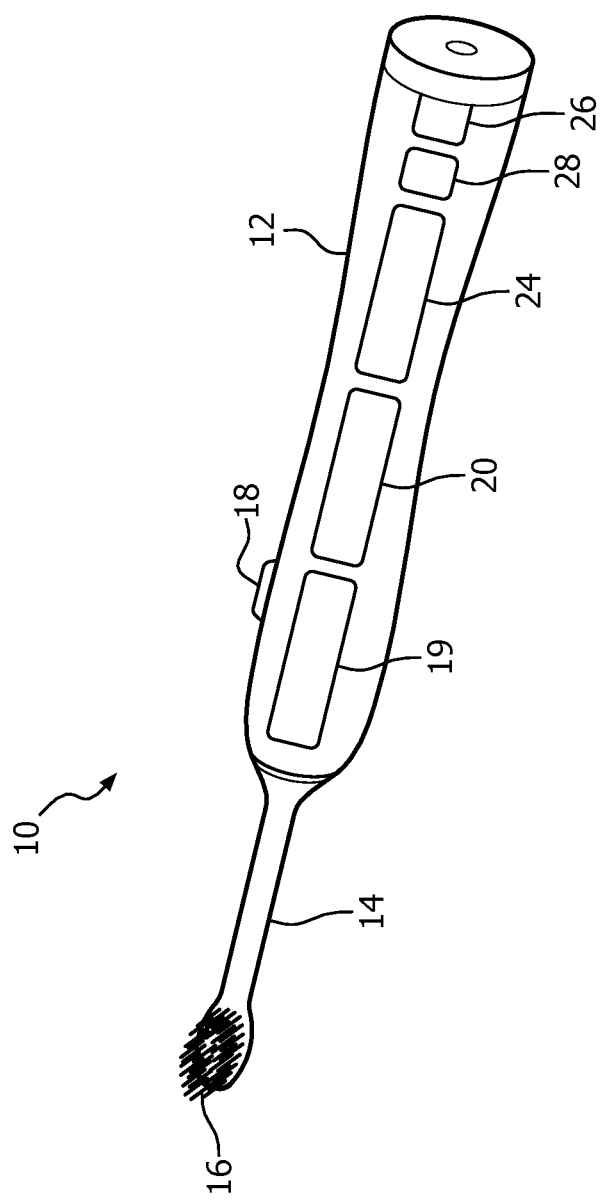
FIG. 1 is an isometric view of a power toothbrush.

FIG. 1 shows a general representation of a power toothbrush 10 which includes a body portion 12 and a removable brushhead portion 14 with a set of bristles 16 at the distal end of the shaft. The power toothbrush includes an on/off switch 18 and interiorly, a motor 19 to drive the brushhead, a rechargeable battery 20 for the motor, a microprocessor 24 for control of the operation of the toothbrush, and a charging coil 26. The toothbrush also includes a force sensor 28. The motor 18 can be selected to produce various brushhead motions, including back-and-forth action over a particular angle, linearly along the axis of the toothbrush, a sweeping motion, or any other action, including a combination of actions. FIG. 1 is intended to be a general representation of a power toothbrush without any particular structural limitations other than described below.

Figure 2:
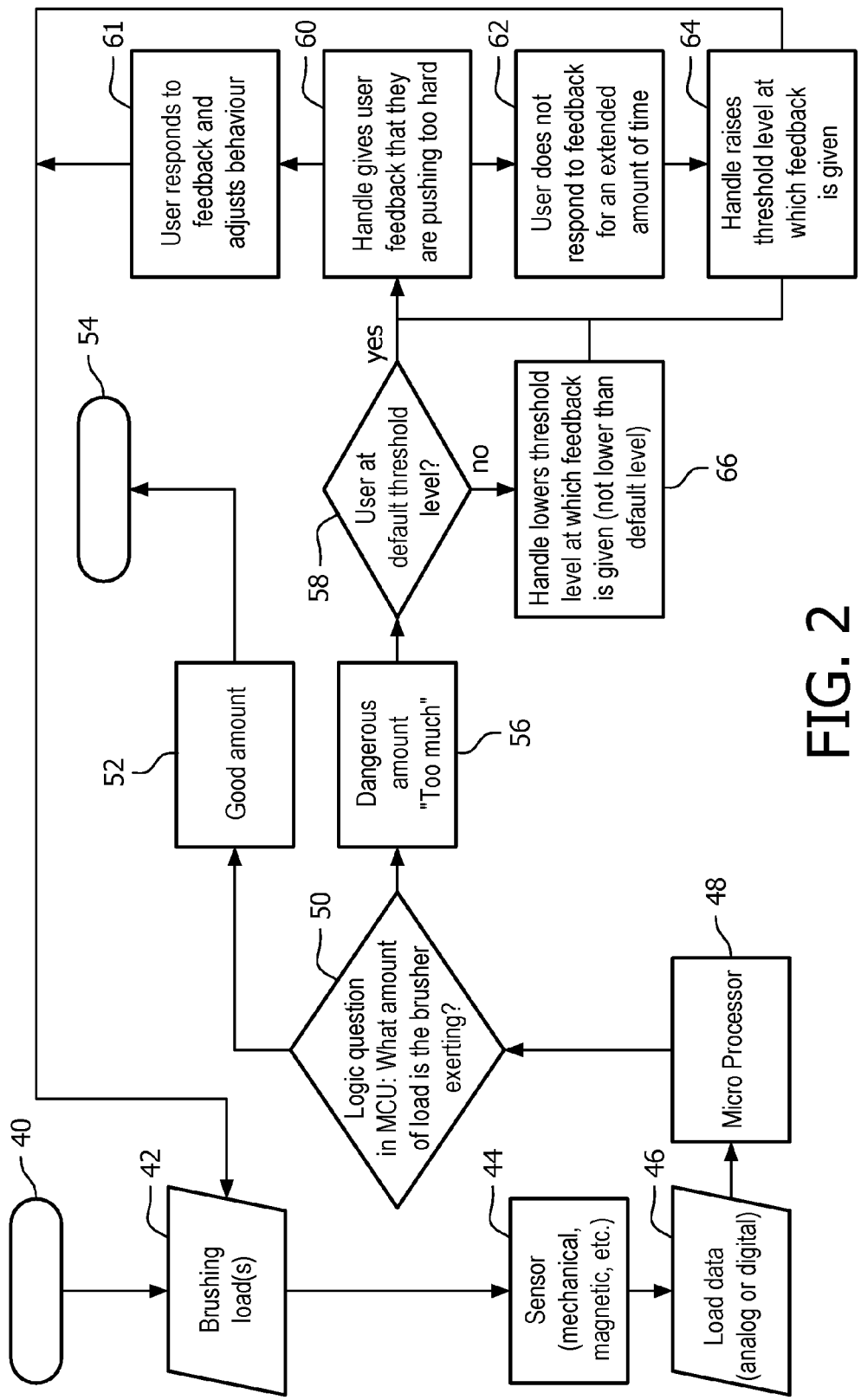
FIG. 2 is a processing diagram which carries out the invention described herein.

FIG. 2 shows a processing sequence/system in the power toothbrush which defines the invention disclosed and claimed herein. The system is a coaching/tutoring tool assisting a user in reducing bristle pressure applied against the teeth. This pressure is referred to as applied load, pressure or force. In the present case, the term "force" is used, with the designation or increments of force being in grams. However, it should be understood that the term "force" used herein covers references to bristle pressure or bristle load on the teeth as well.

The processing sequence begins with user action, designated at block 40. User action refers to the force of the bristles actually applied against the teeth by the user. An actual value of brushing force applied is represented at block 42. The amount of force sensed by a sensor arrangement is shown at block 44. As indicated above, the sensor can take various forms, including for instance, a Hall effect sensor or other known mechanical or magnetic sensor. The particular form of the sensor is not an essential part of the present system, as long as it is accurate. The information can be analog or digital, as shown at block 46 and is transmitted to a microprocessor/controller in the toothbrush. The microprocessor then compares the force data produced by the sensor on the toothbrush with several force levels stored within the microprocessor. Block 50 refers to the functional logic step of comparing the actual force value with threshold values stored in the microprocessor. If the applied force is safe, i.e. an acceptable or "good" value, as shown in block 52, an indication thereof is thereafter provided at 54.

The present arrangement uses visual representations of force levels and thresholds. In the present case, there are three different indications, although they can be varied, i.e. the indications are (1) brushing force is within a "safe" range; (2) the brushing force is above a "harmful" threshold, sometimes referred to as a dangerous level, and (3) the brushing force is at or above one or more intermediate thresholds, indicating "caution" on the part of the user, i.e. a warning to reduce pressure before it reaches a harmful level. In the present case, three different colors are used, green and red, for good and harmful, respectively, and yellow for intermediate or warning. Alternatively, a single color can be used with different shades.

A "good" or safe amount could be, for instance, in the range of 50 grams or more, as long as it does not harm the gums or other tissues.

The logic decision could also indicate that the amount of force is harmful. This could be various amounts, for instance, 300 grams, but it could also be more, depending upon the particular toothbrush arrangement. This is shown at block 56. The next block 58 is directed toward determining whether or not the amount of force has reached a selected initial intermediate level, which is lower than the harmful level, but serves as a warning level relative to approaching extreme pressure. If the answer is yes, meaning that the determined pressure has reached the intermediate level, also referred to as a default level, there is provided an indication to the user that they are applying too much bristle pressure against the teeth, i.e. the user should modify their behavior and decrease the pressure. This is shown at block 60. If the user responds and adjusts the bristle pressure, lowering the force of the bristles against the teeth, the yellow light goes out and the green light comes on (block 61). This indication is fed back to the brushing load block 42.

In some cases, however, the user may not respond by reducing pressure, or even if pressure is somewhat reduced, the pressure is still above the default level, and the yellow light remains on. There is thus no incentive or effective information for the user to change the pressure. In the present case, the processor will determine whether this has continued for an extended period of time, e.g. a selected number of brushing events (block 62). The number of such brushing events can vary; however, one example could be ten consecutive brushing events. The processor in that case collects the actual force values for those brushing events and establishes a mean value. The intermediate/default threshold value is then raised a selected amount, generally the mean value. This step is shown at block 64. With the mean value of pressure, subsequent brushing events will produce a yellow warning light in some cases and in others producing a green light, as the actual pressure/force goes above and below the mean value. The default value is at a level that a small change in pressure will produce a positive result (green light) while if the default were at its initial level, a large change would have been required. The present system provides a distinct positive result for the user, which will encourage continued change as the yellow light intermittently appears.

For subsequent brushing events, when the light is green, not yellow, the threshold will be reduced a small amount, back toward the default level. The amount of reduction can vary, but might be between 20 and 60 grams. This reduction step is shown at block 66. This is, hence, a technique for coaching or encouraging the user to decrease bristle pressure by providing an ability to start at an intermediate level close to where the user is actually operating, so that relatively small change in bristle pressure will have a positive result on the status of the indications. Eventually, with continuing small reductions in the adaptive level, and the user continuing to follow the reduction by further reducing bristle pressure, the user is eventually led or coached back to the default intermediate level. The intermediate level is thus used to accomplish a warning at a predetermined level.

The above system focuses on user action and behavior. In a variation, the structure, material or components of the toothbrush itself can provide the required adjustment to bring bristle pressure back into a safe level. This could be done in various ways, including the changing of amplitude or frequency of the brush when the pressure goes above the default level. When the bristle pressure drops back into a safe area, the frequency and/or amplitude will go to original levels. In another embodiment, the material or structure in the neck or in the bristle plate itself could be chosen and adapted to change in configuration or other ways to reduce the actual force applied against the teeth when the intermediate/default level is indicated. In this case, the toothbrush itself adapts to an indication of high bristle pressure, lowering the bristle pressure. This aspect of the toothbrush can include particular components, the use of "smart" materials, drive train arrangements, housing components, or amplitude and frequency to change actual bristle pressure without any change in user action. This is referred to as an adaptive toothbrush structure.

Accordingly, a system is provided by which a user can be appropriately coached or trained to reduce bristle pressure on the teeth produced by user action, and further, that a toothbrush structure itself can adapt to lower bristle pressure without a change in human action. The adaptive information can be provided continuously to the user, so they can make ongoing adjustments in their behavior (bristle pressure) in order to maintain effective bristle pressure values.

Although a preferred embodiment of the invention has been disclosed for purposes of illustration, it should be understood that various changes, modifications and substitutions may be incorporated in the embodiment without departing from the spirit of the invention, which is defined by the claims which follow.

What is claimed is:

1. An adaptive system for modifying user brushing action, comprising:
    a power toothbrush which includes a system for determining a bristle force applied against a user's teeth;
    a processing system for comparing the determined bristle force against (i) a threshold value of excessive force and (ii) a threshold adaptive value of force which is below the threshold value of excessive force, wherein, the processing system is configured for raising the threshold adaptive value from an initial threshold adaptive value in response to a determined bristle force applied against the user's teeth exceeding the threshold adaptive value for a selected number of brushing events and then for decreasing the threshold adaptive value back toward the initial threshold adaptive value in response to a determined bristle force applied against the user's teeth not exceeding the threshold adaptive value for a further selected number of brushing events; and
    an indication system for communicating information that includes different indications to a user in response to the bristle force applied (i) being at a safe level of force corresponding to an amount of 50 grams or more, as long as the level of force does not arm a user's gums or other tissue, (ii) being at an excessive force corresponding to an amount of 300 grams or more, and (iii) reaching the threshold adaptive value of force.

2. The system of claim 1, wherein the information is communicated to the user continuously.

3. The system of claim 1, wherein the threshold adaptive value is decreased back toward the initial threshold adaptive value in a series of predetermined amounts.

4. The system of claim 3, wherein each amount in the series of predetermined amounts is between 20 and 60 grams.

5. The system of claim 1, wherein the threshold adaptive value is raised from the initial threshold adaptive value to a mean value of the bristle force values determined over several sequential brushing events.

6. The system of claim 5, wherein the several sequential brushing events comprise at least ten.

7. The system of claim 1, wherein the indication system further includes three different light colors, that comprise a first color light associated with the safe level of force, a second color light associated with the excessive level of force, and a third color light associated with the threshold adaptive value of force.

* * * * *